United States Patent [19]

Chowdhary

[11] Patent Number: 5,756,720
[45] Date of Patent: May 26, 1998

[54] DERIVATIZED GUAR GUM COMPOSITION INCLUDING NONIONIC AND CATIONIC GROUPS WHICH DEMONSTRATE EXCELLENT SOLUTION CLARITY PROPERTIES

[75] Inventor: Manjit Singh Chowdhary, Princeton Junction, N.J.

[73] Assignee: Rhodia Inc., Cranbury, N.J.

[21] Appl. No.: 738,290

[22] Filed: Oct. 25, 1996

[51] Int. Cl.$^6$ .............. C07H 1/00; C07H 15/04; C07H 13/04; C08B 37/00
[52] U.S. Cl. .............. 536/124; 536/18.6; 536/114; 536/120; 536/127; 536/119; 536/123.1
[58] Field of Search .............. 536/18.6, 114, 536/120, 124, 127, 119, 123.1

[56] References Cited

U.S. PATENT DOCUMENTS

| | | | |
|---|---|---|---|
| 3,326,890 | 6/1967 | Engelskirchen | 260/209 |
| 3,350,386 | 10/1967 | Engelskirchen | 260/209 |
| 3,483,121 | 12/1969 | Jordan et al. | 252/8.55 |
| 3,912,713 | 10/1975 | Boonstra et al. | 260/209 |
| 4,057,509 | 11/1977 | Costanza et al. | 252/316 |
| 4,169,945 | 10/1979 | Deguia et al. | 536/114 |
| 4,659,911 | 4/1987 | Ryder et al. | 219/521 |
| 4,693,982 | 9/1987 | Carter et al. | 435/274 |
| 4,874,854 | 10/1989 | Colegrove et al. | 536/114 |
| 5,489,674 | 2/1996 | Yeh | 356/114 |
| 5,536,825 | 7/1996 | Yeh et al. | 536/52 |

*Primary Examiner*—John Kight
*Assistant Examiner*—Everett White
*Attorney, Agent, or Firm*—Andrew M. Solomon

[57] ABSTRACT

Nonionic and cationic derivatized guar gum which demonstrates greater than 75% light transmission at a wavelength of from about 500-600 nanometers when dispersed in water in the amount of 0.5 parts per 100 parts water and the process for producing such guar gum is disclosed. The compositions are particularly useful for producing products having utility in personal care and industrial cleaning products.

8 Claims, No Drawings

5,756,720

DERIVATIZED GUAR GUM COMPOSITION INCLUDING NONIONIC AND CATIONIC GROUPS WHICH DEMONSTRATE EXCELLENT SOLUTION CLARITY PROPERTIES

BACKGROUND OF THE INVENTION

1. Field of the Invention

The present invention relates to polygalactomannan compositions and more particularly derivatized guar gum compositions including cationic groups which, when dispersed in water or other solvents to yield a highly viscous solution, are capable of forming a relatively transparent solution. The compositions are particularly useful for applications where clarity and purity of aqueous solutions are desirable such as oil recovery, personal care products, textile chemicals, paper chemicals, paints, and the like.

2. Technology Description

Natural and synthetic polymers containing hydroxy groups have been used as thickeners for foods, coatings, paints, explosive slurries, oil well fluids, cosmetics and other personal care products, and many other functional applications.

One class of polymers that have been widely used as suspending and viscosity agents are polygalactomannans. Polygalactomannans are polysaccharides composed principally of galactose and mannose units and are usually found in the endosperm of leguminous seeds such as guar, locust bean, honey locust, flame tree, and the like. The polygalactomannans may be used in either their natural form or may be substituted with one or more functional groups (e.g., carboxymethyl group). The most commonly used polygalactomannan is guar gum. In practice, to thicken a fluid the polygalactomannans may either be added by themselves, or with other viscosity modifiers such as other polysaccharides, xanthan gum and the like.

While the use of polygalactomannans, and guar gum in particular, as thickening agents has been met with great success, it is still desired to improve the physical properties of the guar gum when dispersed in a solution such as water. One such property is its ability to transmit light when used as an aqueous solution, and particularly one having a high viscosity having uses in personal care applications such as shampoos. Aqueous solutions of guar gum tend to be opaque or translucent at best. It is particularly desired that clear, colorless and less impure solutions be produced when dispersing guar gum in water as it makes the final solution more useful for the above-described applications.

U.S. Pat. No. 4,693,982 discloses the use of enzymes to reduce insolubles in guar gum. The level of clarity produced by the enzymatic treatment is not disclosed in the patent.

U.S. Pat. No. 4,874,854 discloses low viscosity heteropolysaccharides, for example, guar gum. Example 3 discloses a "clarified" guar gum which is produced by cold filtration of a 0.3% solution through diatomaceous earth and precipitated with isopropyl alcohol. The ability of this material to transmit light is not disclosed in the patent.

U.S. Pat. No. 3,912,713 discloses non-lumping derivatives of guar gum produced by derivatizing guar gum splits at a moisture content of 20–80% by weight, raising the moisture content of the splits, if necessary, to 30–80% by weight and fragmenting the splits by pressing them out in a thin layer and drying them on a cylinder heated to 100°–180° C. and comminuting the film to form particulates of a size in the order of +20 mesh, as measured by a Tyler screen, and preferably having a size of 2–5 mm. This process is commonly referred to as drum drying. According to Example 3, the product produced in the Example gives a "clear solution having no lumps or clots on stirring in water". No quantitative definition of "clear" (i.e. light transmittance) is presented in the patent.

U.S. Pat. No. 4,057,509 discloses polygalactomannan allyl ether gels. According to Example 1, guar gum is purified to yield a material having less than 0.1% nitrogen content and about 0.48% ash. The same purification method is described in U.S. Pat. No. 4,169,945.

U.S. Pat. No. 4,659,911 teaches the treatment of 100 parts of guar gum with at least 150 parts of an aqueous alkali solution whereby the water present in the entire solution exceeds 60%. No data regarding the ability of resulting aqueous solutions to transmit light is set forth.

Commonly owned U.S. Pat. Nos. 5,489,674 and 5,536,825 relate to a method for treating polygalactomannan splits to yield a product which, when dissolved in solution at 0.5 weight percent, is able to only provide light transparency, i.e., of greater than 75% at 500–600 nm. The method includes treating the splits in an aqueous alkaline solution followed by washing the splits in water or an organic solvent.

U.S. Pat. Nos. 3,326,890; 3,350,386; and 3,483,121 are directed to methods for producing hydroxyalkyl polygalactomannans by using guar flour as a starting material. Included amongst the teachings is the suspension of guar flour in an organic, water-miscible solvent, and adding an alkaline material and an alkylene oxide to yield the final material.

For use in personal care applications such as soaps, body washes, shampoos and the like, it has been demonstrated that excellent performance benefits can occur when using polymeric materials containing cationic groups. This is particularly true in the case of clear personal compositions having increased viscosities (i.e., greater than about 500 centipoises).

Typically such personal care applications include inorganic salts such as NaCl or $NH_4Cl$ to provide viscosity to the final composition. The use of NaCl is preferred because it provides added viscosity at a low cost without any off odor while being environmentally friendly. For use in combination with NaCl containing personal care products, a preferred cationic polymer has been quaternized hydroxyethyl cellulose. The use of cationic polygalactomannans would be particularly preferred because of their combination of thickening and environmentally friendly properties. However, it has been impossible to use cationic polygalactomannans in the past in conjunction with personal care products including inorganic salts because, when added, they produce a cloudy appearance, making them commercially undesirable.

Accordingly, there exists a need in the art for a derivatized guar gum, particularly one having cationic groups which is capable of producing nearly pure, clear and colorless solutions upon dispersing in water and a novel process for producing the gum.

BRIEF SUMMARY OF THE INVENTION

In accordance with the present invention, cationically derivatized polygalactomannans which are capable of producing nearly pure, clear and colorless solutions upon dispersing in water or an organic solvent, especially those including NaCl, and a novel process for producing them is provided.

One embodiment of the present invention comprises nonionically and cationically derivatized polygalactomannans which demonstrate greater than 75% light transmission at a wavelength of from about 500–600 nanometers when dispersed in water in the amount of 0.5 parts per 100 parts water wherein the cationically derivatized polygalactomannans are produced by the process comprising the steps of:
(a) contacting nonionically derivatized guar flour with an alcohol or an alcohol/water solution;
(b) neutralizing the reaction mixture of step (a) with an acid;
(c) adding a cationic substituent in an amount such that the resulting material has a degree of substitution of the cationic substituent ranging from about 0.20 to about 1.0;
(d) adding an aqueous alkaline solution;
(e) washing the resulting mixture with water, an organic solvent or mixtures thereof; and
(f) recovering the product produced thereby.

In particular embodiments, the polygalactomannan produced includes both nonionic groups and cationic groups having specific molecular substitution and degrees of substitution respectively. In still other embodiments, the polygalactomannan produced may also include anionic groups, yielding an amphoteric material.

Another embodiment of the present invention comprises an oil field chemical, personal care chemical, industrial cleaning chemical, textile chemical, paper chemical or coating composition including the above-described cationically derivatized guar gum.

A third embodiment of the present invention comprises a process for producing a polygalactomannan comprising the steps of:
(a) contacting nonionically derivatized guar flour with an alcohol or an alcohol/water solution;
(b) neutralizing the reaction mixture of step (a) with an acid;
(c) adding a cationic substituent in an amount such that the resulting material has a degree of substitution of the cationic substituent ranging from about 0.20 to about 1.0;
(d) adding an aqueous alkaline solution;
(e) washing the resulting mixture with water, an organic solvent or mixtures thereof; and
(f) recovering the product produced thereby.

Still another embodiment of the present invention comprises a detergent composition useful for cleaning and/or conditioning human hair or skin or cleaning dishes or clothing which contains NaCl or $NH_4Cl$ and further contains a nonionically and cationically derivatized polygalactomannan, the molecular substitution of the nonionic substituent being between about 0.4 and about 1.2 and the degree of substitution of the cationic substituent being between about 0.20 to about 1.0, said composition having a viscosity of greater than about 500 centipoises and said composition having greater than 75% light transmission at a wavelength of from about 500–600 nanometers.

Still another embodiment of the present invention comprises a detergent composition useful for cleaning and/or conditioning human hair or skin or cleaning dishes or clothing which contains NaCl or $NH_4Cl$ and further contains a nonionically, anionically and cationically derivatized polygalactomannan, the molecular substitution of the nonionic substituent being between about 0.14 and about 1.2, the degree of substitution of the anionic substituent being between about 0.10 to about 0.30 and the degree of substitution of the cationic substituent being between about 0.20 to about 1.0, said composition having a viscosity of greater than about 500 centipoises and said composition having greater than 75% light transmission at a wavelength of from about 500–600 nanometers.

Accordingly, it is an object of the present invention to provide a nonionically and cationically derivatized polygalactomannan which easily transmits light when used in an aqueous solution, has a low amount of insolubles, demonstrates excellent crosslinking properties, and can maintain a constant solution viscosity for an extended period of time.

It is another object of the present invention to provide an oil field chemical, food product, personal care or cosmetic chemical, absorbent material, textile chemical, paper chemical or coating composition which includes the novel derivatized polygalactomannan.

A further object of the present invention is to provide a process for making the derivatized polygalactomannan.

A still additional object of the present invention is to provide a detergent composition having excellent solution clarity and high viscosity.

These, and other objects, will readily be apparent to those skilled in the art as reference is made to the detailed description of the preferred embodiment.

DETAILED DESCRIPTION OF THE PREFERRED EMBODIMENT

In describing the preferred embodiment, certain terminology will be utilized for the sake of clarity. Such terminology is intended to encompass the recited embodiment, as well as all technical equivalents which operate in a similar manner for a similar purpose to achieve a similar result.

The present invention relates to novel polygalactomannans and the process for their manufacture. Polygalactomannans are polysaccharides composed principally of galactose and mannose units and are usually found in the endosperm of leguminous seeds, such as guar, locust bean, honey locust, flame tree, and the like. Guar flour, for example, is composed mostly of a galactomannan which is essentially a straight chain mannan with single membered galactose branches. The mannose units are linked in a 1-4-β-glycosidic linkage and the galactose branching takes place by means of a 1–6 linkage on alternate mannose units. The ratio of galactose to mannose in the guar polymer is, therefore, one to two.

Locust bean gum is also a polygalactomannan gum of similar molecular structure in which the ratio of galactose to mannose is one to four. Guar and locust bean gum are the preferred sources of the polygalactomannans, principally because of the commercial availability thereof. In the preferred embodiment, the invention is directed to the production of guar gum.

The preferred guar starting material used in this invention is guar flour, which is often also referred to as guar powder, which has been derivatized with a nonionic substituent.

Preferred nonionic substituents are hydroxyalkyl, wherein alkyl represents a straight or branched hydrocarbon moiety having between 1 and about 6 carbon atoms (e.g., hydroxyethyl, hydroxypropyl, hydroxybutyl, etc.). The substituents are linked to the guar molecule by the reaction of the guar molecule with alkylene oxides (e.g., ethylene oxide, propylene oxide or butylene oxide). This reaction can take place when the guar is in the "splits" or "flour" form and is considered well known by those skilled in the art.

The term "molar substitution" as employed herein is the average number of moles of functional groups per anhydro sugar unit in the polygalactomannan gum. A particularly desired molar substitution of hydroxyalkyl groups is between about 0.01 and about 3.0, more preferably between about 0.14 to about 1.20. If the final polymer produced is cationic in nature, the molar substitution of the hydroxyalkyl groups should be between about 0.40 to about 1.20, even more preferably between about 0.40 to about 0.80 whereas if the final polymer produced is amphoteric in nature, the molar substitution of the hydroxyalkyl groups should be between about 0.14 to about 1.20, even more preferably between about 0.14 to about 0.80. Preferred functional groups are the hydroxyethyl and hydroxypropyl groups.

Also considered within the scope of the invention is to use a starting material which includes one or more anionic groups. In practice the anionic substituent will be a carboxyalkyl group wherein alkyl represents a straight or branched hydrocarbon moiety having between 1 and about 6 carbon atoms. Examples of such substituents include carboxymethyl, carboxyethyl and carboxypropyl groups and the like having a degree of substitution of between about 0.01 and about 3.0. Particularly preferred is the use of a carboxymethyl substituent having a degree of substitution of between about 0.1 and about 0.3.

The term "degree of substitution" as employed herein is the average substitution of functional groups per anhydro sugar unit in the polygalactomannan gum. In guar gum, the basic unit of the polymer consists of two mannose units with a glycosidic linkage and a galactose unit attached to the C6 hydroxyl group of one of the mannose units. On the average, each of the anhydro sugar units contains three available hydroxyl sites. A degree of substitution of three would mean that all of the available hydroxyl sites have been esterified with functional groups.

The above starting materials, and more specifically hydroxypropyl guar gum powder and carboxymethylhydroxypropyl guar gum are commonly available from manufacturers such as Rhône-Poulenc Inc. These materials are considered the starting materials for the present invention.

The starting nonionically substituted guar gum, or nonionically and anionically substituted guar gum in powder form, is then treated with an alcohol or an alcohol/water solution. In practice, the alcohol selected may be methanol, ethanol, isopropanol, n-propyl alcohol, n-butyl alcohol and the like. The alcohols may be used in neat (100%) form or in combination with water, the primary consideration being that the alcohol is miscible with water. Treatment is typically made at ambient temperatures, for example, about 30° C., although the temperature can be increased up to about 70° C. while still obtaining efficacious results.

In practice it is generally preferred to use mixtures of water and organic solvents in this step. Particularly effective results occur when using between about 10 to about 90 percent water by weight and between about 90 to about 10 percent organic solvent by weight. Most preferred is the use of between about 80 to about 90% by weight isopropyl alcohol and between about 10 to about 20% by weight water. For example, excellent results have been obtained wherein the solution selected for use is an isopropanol/water mixture, wherein the respective amounts by weight are 85% isopropanol and 15% water.

The amount of alcohol or alcohol water solution to be used in this step is that amount which is necessary to fully saturate the guar powder. In practice, this amount is usually at least twice the amount by weight of the starting guar powder, and even more preferably, at least three times the amount by weight of the starting guar powder.

The resulting material will typically be alkaline. To improve the clarity obtained when using the final product of the present invention, the alkaline material should be neutralized to a neutral pH (e.g., pH about 7). Any acid may selected for use to neutralize the solution, including strong acids such as hydrochloric acid and sulfuric acid or weak acids such as acetic acid. In a preferred embodiment either hydrochloric or acetic acid is used. The amount of acid used is the amount necessarily for neutralization. Determination of this amount is accomplished by a simple acid/base analysis and is considered well within the skill in the art.

Treatment is typically made at ambient temperatures, for example, about 30° C.

After addition of the alcohol or alcohol/water solution and the subsequent neutralization, followed by agitation as needed, a cationic reagent is added so that the guar gum is derivatized with one or more cationic groups. Cationic substituents include primary, secondary, or tertiary amino groups or quaternary ammonium, sulfonium or phosphinium groups.

Illustrative cationic groups suitable for the practice of the present invention include quaternary ammonium groups. Typical of quaternary ammonium groups are tetramethylammonium chloride and bromide, benzyltrimethylammonium chloride and bromide, tetraethylammonium chloride and bromide, tetrabutylammonium chloride and bromide, methylpyridinium chloride and bromide, benzylpyridinium chloride and bromide, trimethyl-p-chlorobenzylammonium chloride and bromide, and the like, wherein each of the said groups is derivatized in the form of a radical which is substituted in a hydrocolloid gelling agent by means of an alkylene or oxyalkylene linkage.

In preferred embodiments, the quaternary ammonium ether substituents correspond to the formula

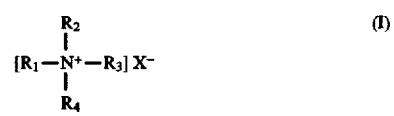

$$[R_1-\overset{R_2}{\underset{R_4}{N^+}}-R_3] X^- \qquad (I)$$

wherein $R_1$ is a monohydroxylated or polyhydroxylated alkyl group containing between one and about six carbon atoms; $R_2$ and $R_3$ are independently, alkyl groups containing between one and about six carbon atoms; $R_4$ is an alkyl group containing between one and about 24 carbon atoms; and X is a halide. The said alkyl groups can contain other atoms such as oxygen, sulfur and halogen.

Specific substituents include 2,3-epoxypropyl N,N,N-trimethylammonium chloride, 3-chloro-2-hydroxypropyl N,N,N-dodecyldimethylammonium chloride, 3-chloro-2-hydroxypropyl N,N,N-cocoalkyldimethylammonium chloride, and 3-chloro-2-hydroxypropyl N,N,N-octadecyldimethylammonium chloride. Such chemicals are commercially available from The Degussa Chemical Company under the trade names QUAB-151, QUAB-342, QUAB-360 and QUAB-426 respectively.

The amount of cationic reagent added to the guar powder is the amount that yields a cationic degree of substitution ranging from about 0.20 to about 1.0, and even more preferably between about 0.23 and about 0.80. Calculation of these amounts is easily obtained by simple stoichiometric equations and is considered well within the skill of the artisan.

To improve the reaction kinetics of the cationic substitution, an alkaline material is added as a catalyst. The alkaline material is typically aqueous solution of base, preferably an aqueous solution containing greater than 12% of NaOH, and more preferably a 12 to 60% aqueous solution of NaOH. Even more preferred is treatment with a 20% to a 50% aqueous solution.

In the preferred embodiment between about 2 and about 50 parts of NaOH (100%) are added for every 100 parts of starting guar flour.

Thereafter, the temperature of the reaction mixture is increased to between about 40 and about 75° C., with a reaction temperature being between about 60 and about 70° C. being even more preferred, and the mixture is stirred for a period of time sufficient to insure complete reaction of the reactants. In practice, this reaction time is between about one and about five hours, with a time of about three hours being more preferred.

Thereafter, the resulting material is neutralized to a neutral pH (e.g., pH about 7). Any acid may selected for use to neutralize the solution, including strong acids such as hydrochloric acid and sulfuric acid or weak acids such as acetic acid. In a preferred embodiment either hydrochloric or acetic acid is used. The amount of acid used is the amount necessarily for neutralization. Determination of this amount is accomplished by a simple acid/base analysis and is considered well within the skill in the art.

After the neutralization, the derivatized guar powder is filtered and then washed with water, an organic solvent, or a mixture of both. Particularly preferred organic solvents are water miscible solvents including alcohols such as methanol, ethanol, isopropanol, n-propyl alcohol, n-butyl alcohol and the like. Other commonly used purification solvents such as acetone, glycols and the like may alternatively be selected. Of the above solvents, the most preferred is the use of methanol, ethanol, isopropyl alcohol, acetone and mixtures thereof.

The volume of the wash liquid is much greater than the amount of treated flour and can be performed in batchwise or multiple applications. In preferred practices the volume of the wash liquid is at least twice the volume of the treated flour and preferably at least three times the volume of the flour. It is preferable to conduct between 2 to 4 independent wash cycles. The concentration of the wash liquid for each cycle can be the same or different. For example washing of the powder may be accomplished by first washing with a dilute isopropyl alcohol solution, followed by washing with stronger solutions of isopropyl alcohol, and finally with acetone.

After washing, the derivatized guar powders are then dried and recovered using means known in the art. Examples of such means include air drying, filtering, evaporative drying, centrifuging, flash grinding, addition of solvents, freeze drying and the like. The use of fluidized bed drying is particularly recommended.

The resulting materials are particularly advantageous in that they are capable of achieving very high clarity when added to water in solution form. When added to water in 0.5% solutions, the inventive materials are capable of producing light transmissions of greater than 75% at 500–600 nm, with water being 100%. By using the inventive process, the guar gum produced can have a light transmission (0.5% solution) of greater than about 80%, more preferably greater than about 90%, and most preferably between about 93% and 100% (with water being 100%).

The compositions are also capable of producing high viscosity solutions while maintaining their clarity. For example a one percent solution of the inventive composition can yield a viscosity of between 300 and about 1000 centipoises using the above process. Increased viscosities can be obtained by conducting the reactions in an inert (e.g., nitrogen) environment.

Because of these above properties, the inventive materials are suitable for a wide range of commercial applications. Included amongst them are in oil and gas recovery, because of the low amount of enzymatic hydrolysis residues, high crosslinking ability, ease of filtration during natural gas recovery and potential synergy with other components such as cross-linking agents; personal care and industrial detergent products, because of low protein content, potentially improved skin sensitivity, clear and colorless appearance for consumer appeal, potential compatibility with other surfactants and personal care chemicals such as polyorganosiloxanes and potential flow modification characteristics; textile chemicals because of potential improved jet flow in textile machinery and increased molecular interaction with xanthan gum; dyes; paper chemicals including print and processing chemicals; paints; food products; explosives; absorbent materials; agricultural products; cosmetics; and any other application where the above combination of high clarity with high viscosity would be beneficial.

In addition, when crosslinked with agents such as borax as discussed above, the inventive compositions are able to provide extremely high crosslinked gels.

A particularly preferred use of the inventive compositions is in personal care compositions, more preferably in shampoos, body washes and in industrial cleaning compositions such as dishwashing detergents, laundry detergents and the like, where the thickening and light transmittance properties of the compositions can advantageously be utilized. In such formulations, the amount of the nonionic and cationic derivatized polygalactomannan to be included is preferably between about 0.1 and about 2.0 percent by weight of the formulation, with amounts between about 0.3 and about 1.5 percent being more preferred and amounts between about 0.5 and about 1.0 percent by weight being most preferred.

In detergent compositions, the formulations used can typically include one or more surfactants in an aqueous carrier. The surfactants selected for use in producing such formulations are considered within the skill of the artisan and can be selected from nonionic, anionic, cationic, amphoteric and zwitterionic surfactants known in the art. Mixtures of the above surfactants may also be selected.

Examples of nonionic surfactants which may be selected include fatty acid amides, alkoxylated fatty alcohol amines, fatty acid esters, glycerol esters, alkoxylated fatty acid esters, sorbitan esters, alkoxylated sorbitan esters, alkylphenol alkoxylates, aromatic alkoxylates and alcohol alkoxylates.

Examples of anionic surfactants which may be selected include alkyl sulfates (alkyl is a fatty alkyl or alkylaryl group), ether sulfates, alkyl sulfonates, sulfosuccinates, sulfosuccinamates, naphthalene formaldehyde condensates, isethionates, taurates, phosphate esters and ether carboxylates.

Examples of cationic surfactants which may be selected include cationic quaternaries such as imidazolines arylalkyl quaternary compounds and aromatic quaternary compounds, amine oxides, and alkoxylated amines.

Examples of amphoteric surfactants which may be selected include betaines, sultaines, glycinates, amphoteric imidazoline derivatives and aminopropionates.

All of the above types of surfactants are commercially available and sold by Rhône-Poulenc Inc.

Also commonly included is an inorganic salt such as NaCl or $NH_4Cl$ to provide thickness to the final formulation. The use of NaCl is preferred because it has an extremely low cost. NaCl is typically present in amounts greater than about 0.5 percent by weight of the final formulation, and typically between about 0.5 to about 5.0 percent by weight of the final formulation, more preferably between about 1.0 to about 3.0 percent by weight of the final formulation. Also expressly considered as falling within the scope of the present inventions are products which utilize $NH_4Cl$ or other inorganic salts in place of NaCl.

However, a significant problem that has occurred in the past when trying to add cationic polygalactomannans to the final formulation of a personal care composition is that the presence of the NaCl (or NH$_4$Cl) interacts with the cationic polygalactomannan resulting in an opaque solution. For aesthetic and market reasons, it is highly desirable to produce a clear formulation. It has been surprisingly discovered that the addition of the cationic polygalactomannans according to the present invention retain a clear appearance while providing added thickness properties. In addition, these materials are biodegradable, environmentally friendly, and mild to human hair and skin. Further, they can enable the production of a superior performing product. For example, shampoos in accordance with the present invention demonstrate superior combing and compatibility results as compared with those using commercially successful cationic polymers.

It has further been surprisingly discovered that only those nonionic and cationic derivatized polygalactomannans having the molecular substitution of the nonionic substituent being between about 0.4 and about 1.2 and the degree of substitution of the cationic substituent being between about 0.20 to about 1.0, or those nonionic, anionic and cationically derivatized polygalactomannans, the molecular substitution of the nonionic substituent being between about 0.14 and about 1.2, the degree of substitution of the anionic substituent being between about 0.10 to about 0.30 and the degree of substitution of the cationic substituent being between about 0.20 to about 1.0 can effectively produce clear solutions when combined with personal care formulations containing NaCl. Compositions which do not have these respective molecular and degree of substitutions yield opaque solutions, making them commercially undesirable.

The formulation may also include optional additives such as perfumes, dyes, natural or synthetic fragrances, conditioning aids, and the like.

The final formulation will have a viscosity of greater than 500 centipoises, preferably between 1000 and about 25000 centipoises and most preferably between about 5000 and about 20000 centipoises. The final formulation will also preferably have a light transmission of greater than about 80%, more preferably greater than about 90%, and most preferably between about 93% and 100%.

The invention will be better understood by reference to the following examples.

EXAMPLE 1

200 grams of JAGUAR® 8060 flour, a hydroxypropyl guar manufactured by Rhône-Poulenc Inc. having a molecular substitution of about 0.4 are added to 1000 ml. of an 85 percent isopropyl alcohol solution. The reaction is stirred for a few minutes and is neutralized with concentrated HCl or glacial acetic acid to neutralize a pH value of 7. Thereafter, 100 gms of 2,3-epoxypropyl N,N,N-trimethylammonium chloride are added over a 15 minute period and the mixture is stirred for an additional 15 minutes. 50 ml of a 50% NaOH solution are added over a 15 minute period and the mixture is stirred for an additional 15 minutes. Thereafter, the mixture is heated to 65° C. and is held at 65° C. for three hours. The mixture is cooled to about room temperature and is neutralized to a pH of about 7 by the addition of glacial acetic acid or HCl. The mixture is filtered and the filtered solids are washed successively with one liter of 50% isopropyl alcohol aqueous solution, one liter of 85% isopropyl alcohol aqueous solution, one liter of 100% isopropyl alcohol, and one liter of acetone. The solids are then dried in a fluidized bed drier at about 60° C. for about one hour.

The resulting composition is a nonionically and cationically derivatized guar gum having a molecular substitution of the nonionic substituent of about 0.4 and a degree of substitution of the cationic substituent of about 0.2. The solution viscosity of a 1% solution at 25° C. is about 300–1500 cps as measured by a Brookfield Viscometer, 20 rpm and the light transmission of a 0.5% aqueous solution at 500–600 nm is greater than 90%.

EXAMPLES 2–29

The procedure of Example 1 is repeated except that different MS and DS values are obtained. Different molecular substitution (MS) values for the hydroxypropyl substituent are obtained by using different starting hydroxypropyl guar materials (in the case where MS=0, guar gum flour is used). Different degree of substitution (DS) values for the cationic substituent are obtained by using appropriate stoichiometric amounts of QUAB-151. The resulting materials are listed in the following Table.

| Example | MS | DS |
|---------|------|------|
| 2 | 0.6 | 0.24 |
| 3 | 0.6 | 0.30 |
| 4 | 0.6 | 0.32 |
| 5 | 0.6 | 0.50 |
| 6 | 0.4 | 0.37 |
| 7 | 0.4 | 0.46 |
| 8 | 0.6 | 0.48 |
| 9 | 0.0 | 0.14 |
| 10 | 0.0 | 0.20 |
| 11 | 0.6 | 0.10 |
| 12 | 0.4 | 0.35 |
| 13 | 0.4 | 0.08 |
| 14 | 0.4 | 0.24 |
| 15 | 0.4 | 0.22 |
| 16 | 0.0 | 0.22 |
| 17 | 0.0 | 0.08 |
| 18 | 0.77 | 0.29 |
| 19 | 0.77 | 0.08 |
| 20 | 0.77 | 0.41 |
| 21 | 0.82 | 0.34 |
| 22 | 0.82 | 0.21 |
| 23 | 0.82 | 0.31 |
| 24 | 0.58 | 0.23 |
| 25 | 0.98 | 0.25 |
| 26 | 0.82 | 0.24 |
| 27 | 0.98 | 0.18 |
| 28 | 0.77 | 0.24 |
| 29 | 0.58 | 0.34 |

FORMULATION DATA AND TESTING

Each of the above Example Compositions are used in shampoo formulations. A first formulation includes the following components (amounts are listed by weight):

Formluation One

| Component | Percent by Weight |
|-----------|-------------------|
| Example Composition | 0.5 |
| Sodium Laureth Sulfate (30% active solution) | 10.0 |
| coconut fatty acid amide (100% active) | 2.5 |
| NaCl | 0, 2.0, 2.5 or 3.0 |
| Water | Q.S. |
| TOTAL | 100 |

The viscosity (in centipoises) and light transmittance (600 nm) for each of the formulations are shown in the following table. As a comparative example, a highly commercially successful polymer commonly used in clear shampoos, which is a quaternized hydroxyethyl cellulose having a molecular substitution of hydroxyethyl groups of 1.2 and a degree of substitution of cationic groups of 0.40 is selected for testing. This comparative example is referenced as CE. Each of the tested shampoos effectively functioned in their cleaning ability. However, their desirability would be limited by a low transmittance value, particularly in the presence of NaCl.

| Ex. | 0% NaCl Vis. | 0% NaCl % T | 2.0% NaCl Vis. | 2.0% NaCl % T | 2.5% NaCl Vis. | 2.5% NaCl % T | 3.0% NaCl Vis. | 3.0% NaCl % T |
|---|---|---|---|---|---|---|---|---|
| CE | 60 | 99 | 4480 | 100 | 6500 | 100 | 9770 | 97 |
| 2 | 0 | 89 | 5230 | 97 | 7330 | 96 | 7280 | 94 |
| 3 | 0 | 99 | 2940 | 96 | 5800 | 96 | 7460 | 97 |
| 4 | 70 | 96 | 5590 | 99 | 8300 | 99 | 10000 | 99 |
| 5 | 20 | 96 | 4640 | 98 | 6680 | 96 | 7900 | 95 |
| 6 | 930 | 85 | 8850 | 95 | 15000 | 95 | 18000 | 93 |
| 7 | not tested | not tested | not tested | not tested | 19000 | 94 | 19000 | 96 |
| 8 | not tested | not tested | not tested | not tested | 14000 | 90 | 16000 | 87 |
| 9 | 820 | 41 | 8520 | 21 | 14000 | 10 | 16000 | 2 |
| 10 | 440 | 1 | 9180 | 12 | 18000 | 18 | 19000 | 24 |
| 11 | 280 | 97 | 7430 | 40 | 11000 | 2 | 13000 | 1 |
| 12 | 969 | 87 | 12000 | 96 | 17000 | 97 | 23000 | 96 |
| 13 | 40 | 99 | 4020 | 52 | 6650 | 2 | 8520 | 2 |
| 14 | 927 | 94 | 9350 | 96 | 16000 | 96 | 21000 | 98 |
| 15 | 893 | 78 | 13000 | 97 | 17000 | 97 | 22000 | 93 |
| 16 | 910 | 50 | 12000 | 64 | 17000 | 69 | 23000 | 73 |
| 17 | 1090 | 92 | 9100 | 2 | 12000 | 4 | 12000 | 6 |
| 18 | 571 | 96 | 8850 | 97 | 15000 | 97 | 22000 | 97 |
| 19 | 711 | 99 | 5760 | 1 | 9440 | 4 | 15000 | 5 |
| 20 | 720 | 93 | 12000 | 96 | 17000 | 96 | 22000 | 96 |
| 21 | 551 | 95 | 8300 | 97 | 14000 | 98 | 17000 | 98 |
| 22 | 721 | 97 | 6900 | 98 | 15000 | 96 | 18000 | 94 |
| 23 | 927 | 96 | 13000 | 96 | 18000 | 98 | 23000 | 99 |
| 24 | 1430 | 96 | 22000 | 98 | 29000 | 98 | 30000 | 98 |
| 25 | 6330 | 96 | 15000 | 89 | 15000 | 91 | 13000 | 67 |
| 26 | 671 | 87 | 9270 | 98 | 15000 | 98 | 17000 | 98 |
| 27 | 782 | 97 | 9020 | 98 | 15000 | 97 | 16000 | 75 |
| 28 | 835 | 97 | 8520 | 97 | 13000 | 95 | 18000 | 94 |
| 29 | 830 | 95 | 12000 | 94 | 16000 | 98 | 19000 | 98 |

A second formulation includes the following components (amounts are listed by weight):

Formluation Two:

| Component | Percent by Weight |
|---|---|
| Example Composition | 0.5 |
| Sodium Laureth Sulfate (30% active solution) | 10.0 |
| cocoamidopropyl betaine (30% active) | 2.5 |
| NaCl | 0, 1.0, 1.5 or 2.0 |
| Water | Q.S. |
| TOTAL | 100 |

The viscosity (in centipoises) and light transmittance (600 nm) for each of the formulations are shown in the following table. As a comparative example, a highly commercially successful polymer commonly used in clear shampoos, which is a quaternized hydroxyethyl cellulose having a molecular substitution of hydroxyethyl groups of 1.2 and a degree of substitution of cationic groups of 0.40 is selected for testing. This comparative example is referenced as CE. Each of the tested shampoos effectively functioned in their cleaning ability. However, their desirability would be limited by a low transmittance value, particularly in the presence of NaCl.

| Ex. | 0% NaCl | 0% NaCl | 2.0% NaCl | 2.0% NaCl | 2.5% NaCl | 2.5% NaCl | 3.0% NaCl | 3.0% NaCl |
|---|---|---|---|---|---|---|---|---|
| CE | 90 | 99 | 1800 | 99 | 4840 | 99 | 16000 | 94 |
| 2 | 0 | 97 | 3110 | 97 | 12000 | 84 | 24000 | 90 |
| 3 | 30 | 98 | 1190 | 97 | 4980 | 95 | 14000 | 96 |
| 4 | 140 | 98 | 3320 | 98 | 10000 | 95 | 18000 | 97 |
| 5 | 100 | 98 | 3460 | 97 | 10000 | 97 | 21000 | 97 |
| 6 | 1110 | 93 | 5110 | 96 | 14000 | 95 | 29000 | 95 |
| 7 | not tested | not tested | not tested | not tested | 16000 | 95 | 36000 | 96 |
| 8 | not tested | not tested | not tested | not tested | 18000 | 82 | 39000 | 80 |
| 9 | 1050 | 43 | 53000 | 15 | 15000 | 7 | 32000 | 2 |
| 10 | 1090 | 3 | 6200 | 18 | 18000 | 25 | 37000 | 17 |
| 11 | 440 | 94 | 4660 | 8 | 9270 | 1 | 33000 | 1 |
| 12 | 1390 | 94 | 6900 | 97 | 18000 | 97 | 38000 | 98 |
| 13 | 140 | 99 | 2610 | 5 | 9100 | 2 | 24000 | 1 |
| 14 | 1390 | 96 | 6210 | 97 | 17000 | 96 | 33000 | 95 |
| 15 | 1120 | 93 | 4830 | 94 | 14000 | 97 | 32000 | 97 |
| 16 | 1180 | 52 | 5860 | 62 | 13000 | 62 | 33000 | 62 |
| 17 | 1430 | 96 | 4480 | 2 | 8430 | 2 | 28000 | 2 |
| 18 | 1010 | 96 | 5040 | 95 | 14000 | 92 | 35000 | 81 |
| 19 | 1030 | 96 | 3420 | 2 | 11000 | 4 | 26000 | 2 |
| 20 | 1040 | 94 | 6500 | 94 | 16000 | 94 | 39000 | 95 |
| 21 | 1080 | 96 | 5460 | 97 | 16000 | 96 | 35000 | 98 |
| 22 | 1030 | 98 | 4790 | 98 | 15000 | 96 | 31000 | 86 |
| 23 | 902 | 97 | 3560 | 98 | 8680 | 98 | 23000 | 98 |
| 24 | 1140 | 97 | 4830 | 96 | 10000 | 80 | 26000 | 62 |
| 25 | 1000 | 98 | 5060 | 98 | 13000 | 85 | 30000 | 74 |
| 26 | 690 | 96 | 3120 | 98 | 7900 | 98 | 17000 | 99 |
| 27 | 860 | 98 | 3520 | 98 | 9200 | 48 | 23000 | 1 |
| 28 | 1120 | 97 | 4510 | 97 | 13000 | 97 | 28000 | 96 |
| 29 | 977 | 96 | 5560 | 98 | 16000 | 98 | 31000 | 98 |

COMB TESTING

To determine if the formulations would effectively provide functional properties to human hair a Diastrom Wet Combing Test is performed on each of the following Formulation Three Samples.

Formluation Three:

| Component | Parts by Weight |
|---|---|
| Example Composition | 10.0 |
| Sodium Laureth Sulfate (30% active solution) | 600.0 |
| cocoamidopropyl betaine (30% active) | 199.0 |
| coconut fatty acid amide (100% active) | 169.0 |
| NaCl | 30.0 |
| Formalin | 2.0 |
| Water | Q.S. |
| TOTAL | 2000 |

This industrial standard test measures the difference between the peak force used to comb treated human hair treated with the experimental shampoos as compared to the peak force used to comb human hair which has only been wetted with water. A working area is obtained by measuring the area under the force curve obtained for the test compositions as compared to that of the water only treated hair. A positive value for both peak value and work value is considered desirable. The results are shown in the following Table.

| Sample | Peak Value | Work Area |
|---|---|---|
| CE | 7 | 11 |
| 2 | not tested | not tested |

-continued

| Sample | Peak Value | Work Area |
|---|---|---|
| 3 | 3 | 7 |
| 4 | 12 | 10 |
| 5 | -1 | 0 |
| 6 | -2 | 0 |
| 7 | 7 | 7 |
| 8 | 5 | -2 |
| 9 | 32 | 32 |
| 10 | 24 | 26 |
| 11 | 31 | 29 |
| 12 | 16 | 17 |
| 13 | 48 | 45 |
| 14 | 12 | 14 |
| 15 | 14 | 12 |
| 16 | 4 | 6 |
| 17 | 49 | 48 |
| 18 | 30 | 26 |
| 19 | 30 | 28 |
| 20 | 3 | -2 |
| 21 | 4 | -2 |
| 22 | 9 | 10 |
| 23 | -7 | -7 |
| 24 | 0 | -1 |
| 25 | 2 | 3 |
| 26 | -8 | -9 |
| 27 | 10 | 12 |
| 28 | 8 | 7 |
| 29 | 6 | 8 |

The above data demonstrates that the molecular substitution of the nonionic substituent being between about 0.4 and about 1.2 and the degree of substitution of the cationic substituent being between about 0.20 to about 1.0, yields a composition having a viscosity of greater than about 500 centipoises and having greater than 75% light transmission at a wavelength of from about 500–600 nanometers. In addition, the resulting personal care compositions have excellent detergency, mildness and combing properties.

EXAMPLE 30

200 grams of carboxymethylhydroxypropyl guar manufactured by Rhône-Poulenc Inc. having a molecular substitution of about 0.2 and a degree of substitution of carboxymethyl groups of about 0.1 are added to 1000 ml. of an 85 percent isopropyl alcohol aqueous solution. The reaction is stirred for a few minutes and concentrated HCl or glacial acetic acid is added to neutralize the pH to a value of 7. Thereafter, 120 grams of 2,3-epoxypropyl N,N,N-trimethylammonium chloride are added over a 15 minute period and the mixture is stirred for an additional 15 minutes. 60 ml of a 5% NaOH solution are added over a 15 minute period and the mixture is stirred for an additional 15 minutes. Thereafter, the mixture is heated to 65° C. and is held at 65° C. for three hours. The mixture is cooled to about room temperature and is neutralized to a pH of about 7 by the addition of concentrated hydrochloric acid or glacial acetic acid. The mixture is filtered and the filtered solids are washed successively with one liter of 50% isopropyl alcohol aqueous solution, one liter of 85% isopropyl alcohol aqueous solution, one liter of 100% isopropyl alcohol, and one liter of acetone. The solids are then dried in a fluidized bed drier at about 60° C. for about sixty minutes.

The resulting composition is a nonionically, anionically and cationically derivatized guar gum having a molecular substitution of the nonionic substituent of about 0.2, a degree of substitution of the anionic substituent of about 0.1, and a degree of substitution of the cationic substituent of about 0.4. The solution viscosity of a 1% solution at 25° C. is 300–1500 cps as measured by a Brookfield Viscometer, 20 rpm, and the light transmission of a 0.5% aqueous solution at 500–600 nm is greater than 90%. It is believed that this composition could effectively be used in personal care or industrial detergent applications which include NaCl and yield a highly viscous clear product.

Having described the invention in detail and by reference to the preferred embodiments thereof, it will be apparent that modifications and variations are possible without departing from the scope of the appended claims.

What is claimed is:

1. A process for producing polygalactomannans which contain both nonionic and cationic groups and demonstrate greater than 75% light transmission at a wavelength of from about 500–600 nanometers when dispersed in water in the amount of 0.5 parts per 100 parts water comprising the steps of:

(a) contacting guar flour containing nonionic groups with an alcohol or an alcohol/water solution;

(b) neutralizing the reaction mixture of step (a) with an acid;

(c) adding a cationic substituent in an amount such that the resulting material has a degree of substitution of cationic groups ranging from about 0.20 to about 1.0;

(d) adding an aqueous alkaline solution;

(e) washing the resulting mixture with water, an organic solvent or mixtures thereof; and (f) recovering the product produced thereby.

2. The process according to claim 1 wherein said nonionic groups comprise hydroxyalkyl groups, wherein alkyl represents a straight or branched hydrocarbon moiety having between 1 and about 6 carbon atoms.

3. The process according to claim 2 wherein said nonionic groups have a molecular substitution between about 0.4 and about 1.2.

4. The process according to claim 1 wherein said cationic groups are quaternary groups.

5. The process according to claim 4 wherein cationic substituents are of the formula

wherein $R_1$ is a monohydroxylated or polyhydroxylated alkyl group containing between one and about six carbon atoms; $R_2$ and $R_3$ are independently, alkyl groups containing between one and about six carbon atoms; $R_4$ is an alkyl group containing between one and about 24 carbon atoms; and X is a halide.

6. The process according to claim 4 wherein said cationic groups have a degree of substitution between about 0.23 and about 0.80.

7. The process according to claim 1 wherein said polygalactomannans further comprise anionic groups.

8. The process according to claim 7 wherein said anionic groups comprise carboxyalkyl groups wherein alkyl represents a straight or branched hydrocarbon moiety having between 1 and about 6 carbon atoms.

* * * * *